United States Patent
Yu et al.

(10) Patent No.: US 9,591,868 B2
(45) Date of Patent: Mar. 14, 2017

(54) METHODS FOR IMPROVING THE CONDITION OF HAIR IN NON-HUMAN ANIMALS

(71) Applicant: Hill's Pet Nutrition, Inc., Topeka, KS (US)

(72) Inventors: Shiguang Yu, Topeka, KS (US); Joseph Greitl, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 14/654,686

(22) PCT Filed: Dec. 20, 2012

(86) PCT No.: PCT/US2012/070749
§ 371 (c)(1),
(2) Date: Jun. 22, 2015

(87) PCT Pub. No.: WO2014/098852
PCT Pub. Date: Jun. 26, 2014

(65) Prior Publication Data
US 2015/0327575 A1   Nov. 19, 2015

(51) Int. Cl.
A23K 1/16 (2006.01)
A61K 31/198 (2006.01)

(52) U.S. Cl.
CPC .......... *A23K 1/1634* (2013.01); *A23K 20/142* (2016.05); *A23K 20/147* (2016.05); *A23K 50/40* (2016.05); *A23K 50/42* (2016.05); *A23K 50/45* (2016.05); *A23K 50/48* (2016.05); *A61K 31/198* (2013.01)

(58) Field of Classification Search
CPC ........................... A23K 1/1634; A23K 31/198
See application file for complete search history.

(56) References Cited

U.S. PATENT DOCUMENTS

| 6,331,569 | B1 | 12/2001 | Kisters et al. | |
|---|---|---|---|---|
| 7,982,066 | B2 | 7/2011 | Scheele | |
| 2004/0131750 | A1* | 7/2004 | Russell | A23J 1/02 426/643 |
| 2008/0182894 | A1 | 7/2008 | Takino et al. | |
| 2009/0298942 | A1* | 12/2009 | Fone | A23K 1/1634 514/561 |
| 2010/0098778 | A1* | 4/2010 | Yamka | A23K 1/1609 424/639 |

FOREIGN PATENT DOCUMENTS

| CN | 1440680 | 9/2003 |
|---|---|---|
| GB | 2322550 | 9/1998 |
| WO | WO95/28854 | 2/1995 |
| WO | WO0132030 | 5/2001 |
| WO | WO2007/031725 | 3/2007 |

OTHER PUBLICATIONS

Burns et al. The Journal of Nutrition, 1982, vol. 112, No. 3, pp. 447-452.*
International Search Report and Written Opinion for International Application No. PCT/US2012/070749 mailed on Feb. 4, 2013.
Jones et al., "Hairs from patients with maple syrup urine disease show a structural defect in the fiber cuticle", J Invest Dermatol., Mar. 1996, 461-464, 106(3). Society for Investigative Dermatology, USA.
Tokunaga et al., "Persistent Hydrophobicity Technology for Damaged Hair by the Highly Absorbent 18-MEA," J. Soc. Cosmet, Chem. Japan, 2011, 45(3);190-198.
Yamada et al., "Research Trends in Remedies for Male Pattern Baldness," Folia Pharmacol, Jpn., 2009, 133:73-77.

* cited by examiner

Primary Examiner — James D Anderson

(57) ABSTRACT

The present invention involves methods for improving the quality of the hair of a non-human animal and for increasing the 18-methyleicosanoic acid content of the hair of a non-human animal comprising feeding to the animal an edible composition comprising an effective amount of an amino acid selected from the group comprising isoleucine, threonine, and mixtures thereof.

13 Claims, No Drawings

METHODS FOR IMPROVING THE CONDITION OF HAIR IN NON-HUMAN ANIMALS

BACKGROUND OF THE INVENTION

From a cosmetic standpoint, the most conspicuous aspect of a non-human animal is its coat, or pelage. A smooth, glossy coat gives an animal an attractive appearance and is pleasing to the touch. It is therefore desirable to provide methods for improving the cosmetic condition of healthy animals.

Methods for improving the cosmetic condition of human hair are widely known. A significant proportion of these methods involve applying a topical composition to the hair, before rinsing with copious amounts of water. Given the exceptionally low tolerance of felines and many other non-human animals for bathing, these methods are unsuitable for routine use in the cosmetic care of animals. There is accordingly a need in the art for more appropriate cosmetic methods.

Mammalian hair shafts comprise a central cortex, which contains high levels of keratin, and an outer cuticle. A lipid layer is covalently bound to the outer surface of the cuticle. The lipid layer is responsible for the hydrophobic properties of hair and contributes to its smoothness. The principle component of the lipid layer is 18-methyleicosanoic acid (18-MEA).

It has been reported that a lack of 18-MEA can give hair a dry, dull appearance. It is therefore desirable to provide a method for increasing the level of 18-MEA present in the hair of non-human animals.

BRIEF SUMMARY OF THE INVENTION

An object of the present invention is to provide a cosmetic method for improving the hair of a non-human animal.

In a first aspect, the present invention provides a method of improving the quality of the hair of a non-human animal comprising feeding to the animal an edible composition comprising an effective amount of an amino acid selected from the group comprising isoleucine, threonine, and mixtures thereof.

Optionally, the isoleucine is in the composition in an amount from 0.2 wt % to 23 wt %.

Optionally, the threonine is in the composition in an amount from 0.2 wt % to 23 wt %.

Optionally, the non-human animal is a companion animal.

Optionally, the companion animal is a cat.

Optionally, improving the quality of the hair comprises an effect selected from the group selected consisting of: increased hair strength, increased hydrophobicity, increased smoothness, decreased swelling, increased lustre and combinations thereof.

Optionally, the composition further comprises a nutrient selected from the group consisting of: proteins, carbohydrates, fats, fibres, and combinations thereof.

Optionally, the composition is a nutritionally complete food.

Optionally, composition comprises a functional ingredient selected from the group consisting of: flavorants, palatants, mouth feel agents, preservatives, emulsifiers, bulking agents, nutritional balancing agents, and mixtures thereof.

Optionally, the composition is a dry composition.

Optionally, the composition is a moist composition.

Optionally, the composition is a semi-moist composition.

In a second aspect, the present invention provides a method of increasing the 18-methyleicosanoic acid content of the hair of a non-human animal comprising feeding to the animal an edible composition comprising an effective amount of an amino acid selected from the group comprising isoleucine, threonine and mixtures thereof, wherein the increase in the 18-methyleicosanoic acid content of the hair results in an improvement of the quality of the hair.

In a third aspect, the present invention provides the use of a composition comprising an effective amount of an amino acid selected from the group consisting of: isoleucine, threonine, and mixtures thereof in improving the quality of the hair of a non-human animal wherein the improvement in quality is an increase in the 18-methyleicosanoic acid content of the hair.

It has been found that feeding a composition comprising an effective amount of isoleucine and/or threonine to a non-human animal increases the 18-MEA content of the animal's hair, thereby improving its cosmetic appearance.

DETAILED DESCRIPTION OF THE INVENTION

The following description of the preferred embodiment(s) is merely exemplary in nature and is in no way intended to limit the invention, its application, or uses.

As used herein, "ppm" (parts per million) refers to ppm by weight, unless otherwise indicated.

An animal in the context of the present invention may be any mammal which is not a human.

The methods of the present invention are cosmetic methods which involve feeding to a non-human animal an edible composition comprising an effective amount of an amino acid. The amino acid is selected from the group consisting of: isoleucine, threonine, and mixtures thereof. It has been surprisingly found that feeding a non-human animal such a composition increases the 18-MEA content of the animal's hair, thereby improving the hair's visual and tactile properties. The methods of the present invention may therefore improve the pelage of the animal.

As used herein, the term "edible composition" refers to any composition which may be safely orally administered to the animal. For example, the composition may be in the form of a tablet or a food. Preferably, the composition is a food. The food is preferably a pet food. The term "food" may refer to snacks, treats, and supplements, as well as food products which provide all or most of the nutrients for the animal, and to other classes of food compositions known in the art. For example, the food may be a daily ration, a treat, a chew, a supplement, or a toy. Preferably, the food is a daily ration. Optionally, the food is a moist food, a semi-moist food, or a dry food. Preferably, the food is a dry food. More preferably, the food is a dry kibble.

An effective amount is an amount of active ingredient which produces an improvement in the cosmetic condition of the animal. The amount of active ingredient required to produce such an improvement will vary depending on a number of factors. These include the dosage regime used and the nature of the animal such as its species, age, sex, neuter status and weight. Typically, the compositions used in the methods of the present invention comprise at least 0.2 wt % of the amino acid.

The amino acids used in the methods of the present invention are selected from the group consisting of: isoleucine, threonine, and mixtures thereof. Isoleucine and threonine are essential amino acids for most mammals, that is, they cannot be biosynthesised and must therefore be ingested. Isoleucine and threonine each have two chiral centers and as such can exist in a number of diastereomeric forms. The amino acids will typically be in the naturally occurring forms found in biological systems; isoleucine will generally be (2S, 3S)-2-amino-3-methylpentanoic acid, and threonine will generally be (2S,3R)-2-amino-3-hydroxybutanoic acid.

The amino acids used in the methods of the present invention are generally present in the composition in the free ampholyte form. Alternatively, the amino acids may be present in the form of orally-acceptable salts, alpha ketones, alpha keto acids, peptides or proteins. Examples of suitable counterions include sodium and potassium.

The methods of the invention improve the quality of the hair of a non-human animal. The methods of the present invention produce an improvement in the cosmetic condition of the hair of the non-human animal. Typically, the methods may improve the visual appearance of the hair of the animal. For example, the methods may improve the gloss, shine and/or lustre of the animal's hair. The methods of the present invention may improve the tactile quality of the care of the non-human animal. For example, the methods may increase the smoothness or tensile strength of the hair. Preferably, the methods improve both the visual and tactile qualities of hair. The methods may improve the cosmetic condition of the pelage of the animal.

Preferably, the animal is a companion animal. As used herein, the term "companion animal" refers to any non-human animal which is suitable for being kept as a pet in a domestic setting. Examples of companion animals include cats, dogs, ferrets, rabbits and rodents such as hamsters, guinea pigs, rats and the like. Preferably, the companion animal is a cat or a dog. Most preferably, the companion animal is a cat. As used herein, the term "cat" is synonymous with the term "feline" and refers to domestic cats or house cats. The term "dog" is synonymous with the term "canine".

The methods of the present invention preferably provide a cosmetic effect selected from the group consisting of: increased hair strength, increased hydrophobicity, increased smoothness, decreased swelling, increased lustre, and combinations thereof. These parameters may be measured using any suitable technique known in the art including but not limited to the Miniature Tensile Tester, the Tensiometer based on the Wilhelmy balance principle, comb resistance using Dia-Stron, transverse hair measurement using Laser Scan Micrometer and the Gloss Meter.

The compositions used in the methods of the present invention preferably comprise a food ingredient selected from the group consisting of: proteins, carbohydrates, fats, dietary fibers, mineral mixture, vitamin mixture, and combinations thereof.

The skilled person would be aware of appropriate quantities of the food ingredients. The composition typically includes a mixture of food ingredients in various proportions. For example, the food composition may include fat in an amount from 0 wt % to 50 wt % fat, or carbohydrate in an amount from 0 wt % to 75 wt %, or protein in an amount from 0 wt % to 95 wt %, or dietary fiber in an amount from 0 wt % to 40 wt % dietary fiber, or mineral mixture in an amount from 0 wt % to 10 wt %, or vitamin mixture in an amount from 0 wt % to 5 wt %, or any combination thereof.

The composition preferably comprises, by weight of the composition, protein in an amount from 30 wt % to 40 wt %, fat in an amount from 5 wt % to 15 wt %, carbohydrate in an amount from 40 wt % to 50 wt %, fiber in an amount from 0 wt % to 10 wt, mineral mixture in an amount from 0 wt % to 0.1 wt %, and vitamin mixture in an amount from 0 wt % to 0.2 wt %. More preferably the composition comprises, by weight of the composition, 35 wt % protein, 9 wt % fat, 44 wt % carbohydrate, 5 wt % fiber, 0.05 wt % mineral mixture and 0.15 wt % vitamin mixture.

Protein may be supplied by any of a variety of sources known by those skilled in the art, including plant sources, animal sources, or both.

Vegetable protein sources suitable for preparing compositions of the invention include, but are not limited to, potato concentrate, soy concentrate, soy protein isolate, soybean meal, corn gluten meal, rice protein isolate, pea protein concentrate, wheat protein concentrate, and wheat protein isolate. Vegetable protein may be isolated from any portion of a plant, isolated from more than one portion of a plant, and isolated from more than one plant by methods known by those of skill in the art. Vegetable protein may also be concentrated by methods known by those of skill in the art.

Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. The protein content of foods may be determined by any number of methods known by those of skill in the art, for example, as published by the Association of Official Analytical Chemists in *Official Methods of Analysis* ("OMA"). The amount of "crude protein" in a composition disclosed herein may be determined based on the amount of nitrogen in the composition according to methods familiar to one of skill in the art.

Carbohydrate may be supplied by any of a variety of sources known by those skilled in the art, including oat fiber, cellulose, peanut hulls, beet pulp, parboiled rice, corn starch, corn gluten meal, and any combination of those sources. Grains supplying carbohydrate include, but are not limited to, wheat, corn, barley, and rice. Carbohydrate content of foods may be determined by any number of methods known by those of skill in the art. Generally, carbohydrate percentage may be calculated as nitrogen free extract ("NFE"), which may be calculated as follows: NFE=100%—moisture %—protein %—fat %—ash %—crude fiber %.

Fat can be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The fat content of a composition may be determined by any number of methods known by those of skill in the art.

Dietary fiber refers to the components of plants which are resistant to digestion by the animal's digestive enzymes. The dietary fiber content of a composition may be determined by any number of methods known by those of skill in the art, such as those published by the OMA. Dietary fiber includes soluble and insoluble fiber.

Soluble fiber is resistant to digestion and absorption in the small intestine but undergoes complete or partial fermentation in the large intestine. Examples of soluble fiber sources include beet pulp, guar gum, chicory root, psyllium, pectin, blueberry, cranberry, squash, apples, oats, beans, citrus, barley, and peas. Insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, e.g., hulls of grains such as rice, corn, and beans. The crude fiber content of a composition may be determined by any number of methods known by those of skill in the art.

The composition is preferably a nutritionally complete food. A nutritionally complete food is a food that includes sufficient nutrients for maintaining the health of a healthy animal. Nutritional requirements vary between animals. One of ordinary skill in the art can select the amount and type of food ingredients needed based upon the dietary requirements of the animal as determined by the animal's species, age, size, weight, health, function, etc. Typically, the nutritionally complete composition will be a pet food suitable for a companion animal. Guidance may be found in, for example, the Official Publication of The Association of American Feed Control Officials, Inc. (AAFCO), Atlanta, Ga., 2012, or the National Research Council's *Nutrient Requirements of Dogs and Cats*, The National Academy Press, Washington, D.C., 2006.

Optionally, the compositions used in the methods of the present invention comprise at least one functional ingredient which is suitable for consumption by a healthy animal. Functional ingredients may, for example, improve the storage characteristics of the composition, enhance the palatability of a composition, or provide a nutritional benefit to the animal. Examples of functional ingredients include fillers, binding agents, stabilizers, emulsifiers, buffers, flavorants, colourants, palatants, salts, and nutritional balancing agents. Other examples of functional ingredients include meat analogues, walnut oil, sesame oil, sunflower oil, capsibiol-T, pomegranate, magnolia, lipoic acid, ginger, green tea and black tea.

The at least one functional ingredient may be present in the composition in an amount from 0% to 15% by weight of the composition. Optionally, the function ingredient is present in the composition in an amount from 0% to 5% by weight of the composition. Nutritional balancing agents are preferably present in an amount from 0% to 2.0% by weight of the composition and more preferably in an amount from 0% to 1.0% by weight of the composition.

Examples of suitable binding agents include sodium alginate, gum arabic, sodium carboxy ethyl cellulose, guar gum, xanthan gum, maltodextrin, gelatinized starch, soy protein binders and the like.

A buffer may be used to control the pH of the composition. The pH may, for example, be selected so as to inhibit spoilage. The buffer may comprise a weak acid and/or a weak base. Any food-safe acid or base may be used, e.g. phosphoric acid, maleic acid, citric acid, or acetic acid.

Flavorants may be used to enhance the palatability of the composition. Examples of flavorants include dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Other illustrative flavorants include peppermint, peppermint menthol, eucalyptol wintergreen, licorice, cloves, cinnamon, spearmint, cherry, lemon, orange, lime, menthol and various combinations thereof.

The compositions optionally comprise a nutritional balancing agent. Examples of nutritional balancing agents include antioxidants, vitamins, fatty acids, minerals and trace elements. The Association of American Feed Control Officials, Inc. provides recommended amounts of such nutrients for dogs and cats.

Useful vitamins may include, but are not limited to, vitamin A, vitamin $B_1$, vitamin $B_2$, vitamin $B_6$, vitamin $B_{12}$, vitamin C, vitamin D, vitamin E, vitamin H (biotin), vitamin K, folic acid, inositol, niacin, and pantothenic acid.

The composition may contain fatty acids, such as eicosapentaenoic acid (EPA), n-3 and n-6 fatty acids. Fatty acids may be present in an amount from of 0.05% to 5% by weight of the composition. n-3 fatty acids may be present in an amount from 0.0001% to 2% by weight of the composition. n-6 fatty acids may be present in an amount from 0.5% to 5% by weight of the composition.

The food compositions used in the present invention may optionally comprise a meat analogue. The term "meat analogue" denotes textured protein resembling meat which may be cut into pieces, having the appearance of whole meat pieces. Meat analogues may comprise vegetable protein sources such as soybean, wheat, cottonseed, sunflower seed, and corn. Other protein sources such as fish meal, keratin, algae and kelp may also be included in meat analogues. Additionally, meat analogues may further comprise meat or meat by-products, including chicken, turkey, beef, and pork. The meat analogues may still further comprise meat flavors, spices, fat, synthetic fat, animal tissue and other materials which make them more "meat-like."

Preferably, the compositions used in the methods of the present invention comprise isoleucine, threonine, or mixtures thereof in an amount from 0.2 wt % to 23 wt % isoleucine and/or from 0.2 wt % to 23 wt % threonine. More preferably, the compositions used in the methods of the present invention comprise isoleucine, threonine, or mixtures thereof in an amount from 0. wt % to 3 wt % isoleucine and/or from 0.5 wt % to 2.5 wt % threonine.

Optionally, the compositions using the methods of the present invention are dry compositions. Dry compositions comprise less than 15% moisture. Preferably, dry compositions have a moisture content from of from 3% to 11% by weight of the composition.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavours, fats, oils, powders, and the like. Kibble also can be made from the dough using a baking process, rather than extrusion, wherein the dough is placed into a mold before dry-heat processing.

The compositions may also be designed to be easier to chew. Canine and feline foods are typically formulated based on life stage (age), size, body composition, and breed. The compositions may be formulated to address the specific nutritional differences of senior regular or small breed dogs, large breed dogs, and cats.

The dry compositions preferably comprise at least 28 wt % protein and at least 9 wt % fat of the composition.

Optionally, the compositions used in the methods of the present invention are moist compositions. Moist compositions have a moisture content from of from 60% to 90% or greater by weight of the composition. Moist compositions which are suitable for use in the methods of the present invention may be prepared using conventional food preparation processes known to skilled artisans. For example, ground animal proteinaceous tissues are mixed with the other ingredients such as fish oils, cereal grains, balancing ingredients, functional ingredients (e.g., vitamin and mineral mixtures, inorganic salts, cellulose and beet pulp, bulking agents, and the like) and water in amounts sufficient for processing to form a mixture. These ingredients are mixed in a vessel suitable for heating while blending the components. Heating of the mixture is effected using any suitable manner, for example, direct steam injection or using a vessel fitted with a heat exchanger. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. The amino acid may be added to the compositions before, during, or after preparation.

The moist compositions preferably comprise at least 6 wt % protein and at least 3 wt % fat, of the composition. For example, a moist composition may comprise protein in an amount from 5 wt % to 8 wt % and fat in an amount from 3 wt % to 13 wt %.

Optionally, the compositions used in the methods of the present invention may be semi-moist compositions. "Semi-moist" refers to compositions with a moisture content from of from 25% to 35% by weight composition. Such compositions may be prepared using techniques known in the art. Also contemplated herein are compositions that may comprise components of various consistencies as well as components that may include more than one consistency, for example, soft, chewy meat like particles as well as kibble having an out of cereal component and an inner cream component.

The semi-moist compositions preferably comprise at least 18 wt % protein and at least 10 wt % fat, of the composition. For example, a semi-moist composition may comprise protein in an amount from 18 wt % to 25 wt % and fat in an amount from 10 wt % to 15 wt %.

In a further aspect, the present invention provides the use of a composition comprising an effective amount of an amino acid selected from the group consisting of: isoluceine, threonine, and mixtures thereof in improving the quality of the hair of a non-human animal, wherein the improvement in quality is an increase in the 18-methyleicosanoic acid content of the hair.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

Effects of Isoleucine and Threonine Supplementation in Healthy Cats

The incorporation of supplemental isoleucine and threonine into the diet of healthy cats was found to improve the condition of their hair, as represented by an increase in the 18-methyleicosanoic acid (18-MEA) content of the hair.
Materials and Methods The hair was clipped from the left middle flank areas of 24 healthy adult cats. The clipped regions measured approximately 20.32 cm by 10.16 cm (about 8 inches by about 4 inches). Hair was clipped as close to the skin as possible. The cats were then fed a base diet consisting of a commercially available nutritionally complete food for a period of 90 days. The nutrient content of the base food is set out in Table 1.

TABLE 1

| Nutrient | Weight % |
| --- | --- |
| Crude Protein | 34.0 |
| Crude Fat | 9.6 |
| Carbohydrate (NFE) | 34.1 |
| Crude Fiber | 6.4 |
| Ash | 5.8 |
| Magnesium | 0.1 |
| Chloride | 0.7 |
| Calcium | 1.0 |
| Phosphorous | 0.8 |
| Potassium | 0.6 |
| Sodium | 0.3 |

On day 90, newly grown hair was clipped from the left middle flanks of the cats. The clipped regions measured approximately 19.05 cm by 8.89 cm (about 7.5 inches by about 3.5 inches). Samples of the clipped hair from each cat were retained and analysed for their 18-MEA content in order to determine the base line levels.

The cats were divided into four groups of 6. The age, sex and nurturing status of the cats were balanced between the groups. The groups were randomly assigned a diet selected from the base diet, the base diet plus supplemental leucine, the base diet plus supplemental isoleucine, and the base diet plus supplemental threonine as shown in Table 2.

TABLE 2

| Diet | Amt in food (Control) | Added isoleucine | Added leucine | Added threonine |
| --- | --- | --- | --- | --- |
| Isoleucine (%) | 1.3 | 2.3 | 1.3 | 1.4 |
| Leucine (%) | 3.2 | 3.6 | 4.5 | 3.4 |
| Threonine (%) | 1.1 | 1.1 | 1.3 | 2.3 |

The groups were fed the assigned diets for 90 days.

On day 180, the newly grown hair was clipped from the left middle flanks of the cats. The clipped regions measured approximately 17.78 cm by 7.62 cm (about 7 inches by about 3 inches). Samples of clipped hair from each cat were retained and analysed for 18-MEA content.

For the 18-MEA analysis, hair samples were first washed with circulating ethyl ether for 6 hours to remove the surface lipids and oils. The hair samples were cut into pieces about 5 mm in length or less, digested and extracted for 18-MEA that was measured with a gas chromatograph.

The 18-MEA data were analysed using a regression model. Hair 18-MEA content was the dependent variable, and diet was used as the independent variable. The base line data were used as the covariant.

Results and Discussion

The average 18-MEA contents of the hair of each group of cats at the end of the treatment are set out in Table 3.

TABLE 3

| Diet | Hair MEA concentration/mg/g |
|---|---|
| Control | 10.9 |
| Isoleucine supplemented | 11.5 |
| Leucine supplemented | 11.1 |
| Threonine supplemented | 11.7 |

The data shows that isoleucine and threonine each significantly increased the 18-MEA concentration of the hair ($p<0.05$). Leucine produced no significant effect ($p>0.05$). Increased concentrations of 18-MEA in the hair may produce a number of cosmetic benefits. These include increase hair strength, increased hydrophobicity, increased lustre and decreased swelling.

As used throughout, ranges are used as shorthand for describing each and every value that is within. Any value within can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages expressed herein are by weight of the composition unless specifically stated otherwise.

What is claimed is:

1. A method of improving the quality of hair of a non-human animal lacking 18-methyleicosanoic acid in the hair comprising feeding to the non-human animal in need thereof an edible composition comprising an effective amount of threonine to increase 18-methyleicosanoic acid in the hair and improve the quality of the hair of the non-human animal, wherein improving the quality of the hair is evidenced by an improvement selected from: increased hair strength, increased hydrophobicity, increased smoothness, decreased swelling, increased luster, and combinations thereof.

2. A method of increasing 18-methyleicosanoic acid of the hair of a non-human animal lacking 18-methyleicosanoic acid in the hair comprising feeding to the non-human animal in need thereof an edible composition comprising an effective amount of threonine to increase 18-methyleicosanoic acid of the hair, wherein the increase in the 18-methyleicosanoic acid of the hair results in an improvement of the quality of the hair.

3. The method of claim 1 wherein the edible composition further comprises an effective amount of isoleucine.

4. The method of claim 3, wherein the isoleucine is in the composition in an amount from 0.2 wt % to 23 wt %.

5. The method of claim 1, wherein the threonine is in the composition in an amount from 0.2 wt % to 23 wt %.

6. The method of claim 1, wherein the non-human animal is a companion animal.

7. The method of claim 6, wherein the companion animal is a cat.

8. The method of claim 1, wherein the composition further comprises a food ingredient selected from: proteins, carbohydrates, fats, fibres, and combinations thereof.

9. The method of claim 8, wherein the composition is a nutritionally complete food.

10. The method of claim 1, wherein the composition further comprises a functional ingredient selected from: flavorants, palatants, mouth feel agents, preservatives, emulsifiers, bulking agents, nutritional balancing agents and mixtures thereof.

11. The method of claim 1, wherein the composition is a dry composition.

12. The method of claim 1, wherein the composition is a moist composition.

13. The method of claim 1, wherein the composition is a semi-moist composition.

* * * * *